(12) United States Patent
Woolard et al.

(10) Patent No.: US 8,580,707 B2
(45) Date of Patent: Nov. 12, 2013

(54) USE OF ABSCISIC ACID ON ORNAMENTAL PLANTS

(75) Inventors: Derek D. Woolard, Zion, IL (US); Peter D. Petracek, Grayslake, IL (US); Craig Campbell, Ocoee, FL (US)

(73) Assignee: Valent BioSciences Corporation, Libertyville, IL (US)

( * ) Notice: Subject to any disclaimer, the term of this patent is extended or adjusted under 35 U.S.C. 154(b) by 775 days.

(21) Appl. No.: 12/011,856

(22) Filed: Jan. 30, 2008

(65) Prior Publication Data

US 2008/0227645 A1 Sep. 18, 2008

Related U.S. Application Data

(60) Provisional application No. 60/898,469, filed on Jan. 31, 2007.

(51) Int. Cl.
*A01N 3/02* (2006.01)
*A01N 37/42* (2006.01)
*A01N 37/06* (2006.01)

(52) U.S. Cl.
USPC ................ 504/114; 504/320; 504/171

(58) Field of Classification Search
USPC .................... 504/321, 114, 320, 171
See application file for complete search history.

(56) References Cited

U.S. PATENT DOCUMENTS 5,173,106 A * 12/1992 Kamuro et al. ............... 504/320
2003/0074692 A1 4/2003 Wang et al.

FOREIGN PATENT DOCUMENTS

JP          05058803 A  *  3/1993
WO    WO 2007/008580 A1     1/2007

OTHER PUBLICATIONS

Heschel, M. Shane, Population of differentiation for Abscisic Acid Reponsiveness in Impatiens, International Journal of Plant Sciences, 2001, Abstract.*
Sharma, N., Evaluation of Abscisic Acid Analogs as Holding Agents for Bedding Plant Seedlings, Jan.-Mar. 3006, HortTechnology, vol. 16, Issue 1, pp. 71-77.*
Cornish, K., Role of ABA in Stress-Induced Reductioin of Water Loss From Potted Chrysanthemum Plants, 1985, Growth Regulators in Floriculture, Acta Horticulturae, pp. 381-386.*
Kamuro, Y., Preserving Agent for Cut Flower of Chrysanthemum, Sep. 1993, Patent Abstracts of Japan, 1 page.*
Gibson, J.L., Abscisic Acid Drenches Improve Postproduction Self Life of Impatiens, Jun. 2006, HortScience, vol. 40, Issue 3, pp. 511-512.*
Sharma, N., Evaluation of Abscisic Acid Analogs as Holding Agents for Bedding Plant Seedlings, Jan.-Mar. 2006, HortTechnology, vol. 16, Issue 1, pp. 71-77.*
Krizek et al., "Role of water stress and abscisic acid in modifying sulfur dioxide sensitivity in coleus", Coleus-Blumei, Hortscience 1983, vol. 18, p. 604.
Cutler et al., "Formation and breakdown of ABA", Elsevier Science Ltd., Dec. 1999, vol. 4 No. 12, pp. 472-478.
Krizet et al., "Influence of soil moisture stress and abscisic acid pretreatment in modifying SO2 sensitivity in poinsettie", J. Amer. Soc. Hort. Sci. 1986, 111(3), pp. 446-450.
Mutui et al., "Effects of thidiazuron, ethylene, abscisic acid and dark storage on leaf yellowing and rooting of Pclargonium cuttings", Journal of Horticultural Science and Biotechnology 2005, 80(5), pp. 543-550.
Rajapakse et al., "Transpiration and water use of potted floricultural plants under low-light conditions", J. Amer. Soc. Hort. Sci., 1988, 113(6), pp. 910-914.
EP Search Report issued Dec. 13, 2011.
Grossnickle et al., "Performance of interior spruce seedlings treated with abscisic acid analogs", Can. J. For. Res. vol. 26, 1996, pp. 2061-2070, XP008088662.
Blanchard et al., "Exogenous applications of abscisic acid improved the postharvest drought tolerance of several annual bedding plants", Journal of International Society for Horticultural Science, 2007, XP002664684.
Heschel et al., "Population differentiation for abscisic acid responsiveness in impatiens capensis (balsaminaceae)", Int. J. Plant Sci. 162(6), 2001, pp. 1253-1260, XP009154460.
Xu et al., "Effects of epibrassinolide and abscisic acid on sorghum plants growing under soil water deficit", Jpn. J. Crop Sci., 63(4), 1994, pp. 676-681, XP007919829.
Xu et al., "Effects of epibrassinolide and abscisic acid on sorghum plants growing under soil water deficit", Jpn. J. Crop Sci., 63(4), 1994, pp. 671-675, XP007919830.

* cited by examiner

*Primary Examiner* — John Pak
*Assistant Examiner* — Andriae M Holt
(74) *Attorney, Agent, or Firm* — Wood, Phillips, Katz, Clark & Mortimer

(57) ABSTRACT

The present invention describes a method for increasing the drought tolerance of selected ornamental plants comprising administering abscisic acid (ABA) or its salts to said plants.

4 Claims, No Drawings

USE OF ABSCISIC ACID ON ORNAMENTAL PLANTS

FIELD OF THE INVENTION

The present invention relates to a method of delaying the wilting of drought stressed ornamental plants.

BACKGROUND OF THE INVENTION

Abscisic acid (ABA) is a natural occurring hormone found in all higher plants (Cutler and Krochko. 1999. Trends in Plant Science. 4: 472-478.; Finkelstein and Rock. 2002. The *Arabidopsis* Book. ASPB, Monona, Md., 1-52). ABA is involved in many major events of plant growth and development including dormancy, germination, bud break, flowering, fruit set, growth and development, stress tolerance, ripening, abscission and senescence. One of the roles of ABA is the regulation of water relations in plants through the control of stomata opening and closure.

Most plants have improved drought tolerance following application of ABA, but plants differ in their sensitivity to applied ABA. Different types of ornamental plants differ in both the extent of increased drought tolerance and potential for undesirable side effects from ABA treatment. Others have reported ABA effects on transpiration of whole plants or excised plant parts and yellowing of excised plant parts. Foliar application of ABA reduced the transpiration of potted Poinsettia plants (Krizek, et al., 1986, Influence of soil moisture and ABA acid pretreatment in modifying $SO_2$ sensitivity in poinsettia, J. Amer. Hort. Sci. 111:446-450). ABA applied through the petiole of excised Coleus leaves reduces their transpiration rate compared to excised leaves standing in water (Rajapakse, et al., 1988, Transpiration and water use of potted floricultural plants under low light conditions, J. Amer. Hort. Sci. 113:910-914). Treatment of Geranium cuttings causes the undesirable effect of leaf yellowing (Mutui et al., 2005, Journal of Horticultural Science & Biotechnology 80: 453-550). There are no previous reports that could be used to determine which ornamental plants benefit from ABA application in terms of reduced transpiration rates without unacceptable risk of ABA-induced leaf yellowing or abscission.

SUMMARY OF THE INVENTION

The present invention is directed to the treatment of an ornamental plant selected from the group consisting of Celosia, Chrysanthemum, Coleus, Cosmos, Cuphea, Dianthus, Euryops, Hydrangea, Impatiens, Lantana, Marigold, New Guinea Impatiens, Pentas, Petunia, Salvia and Snapdragon to improve drought tolerance with only slight potential for undesirable side effects comprising applying an effective amount of ABA or a salt thereof to said plants.

DETAILED DESCRIPTION OF THE INVENTION

The applied concentration of ABA can vary widely depending on the water volume applied to plants as well as other factors such as the plant age and size, and plant sensitivity to ABA, but is generally in the range of about 1 ppm to about 10,000 ppm, preferably from about 10 to about 1000 ppm.

It is also contemplated that salts of ABA may be utilized in accordance with the present invention.

As used herein, the term "salt" refers to the water soluble salts of ABA. Representative such salts include inorganic salts such as the ammonium, lithium, sodium, calcium, potassium and magnesium salts and organic amine salts such as the triethanolamine, dimethylethanolamine and ethanolamine salts.

Other ingredients such as surfactants can be used in compositions useful in the present invention.

The presently preferred surfactant for ABA performance is Brij 98 (polyoxyethylene (20) oleyl ether) available from Uniqema (Castle, Del.). Other surfactants that are also useful in the present invention, including but not limited to other surfactants in the Brij family (polyoxyethylene fatty alcohol ether) from Uniqema (Castle, Del.); surfactants in the Tween family (Polyoxyethylene sorbitan esters) from Uniqema (Castle, Del.); Silwet family (Organosilicone) from Union Carbide (Lisle, Ill.); Triton family (Octylphenol ethoxylate) from The Dow Chemical Company (Midland, Mich.); Tomadol family (ethoxylated linear alcohol) from Tomah3 Products, Inc. (Milton, Wis.); Myrj family (Polyoxyethylene (POE) fatty acid esters) from Uniqema (Castle, Del.); Span family (Sorbitan ester) from Uniqema (Castle, Del.); Trylox family (Ethoxylated Sorbitol and Ethoxylated Sorbitol Esters) from Cognis Corporation (Cincinnati, Ohio). These surfactants, commercially available for agricultural use, are also useful in the present invention: Latron B-1956 (77.0% modified phthalic/glycerol alkyl resin and 23.0% Butyl alcohol) from Rohm & Haas (Philadelphia, Pa.); Caspil (Blend of Polyether-polymethylsiloxanecopolymer and nonionic surfactant) from Aquatrols (Paulsboro, N.J.); Agral 90 (Nonyl phenol ethoxylate) from Norac Concept. Inc. (Orleans, Ontario, Canada); Kinetic (99.00% proprietary blend of polyalkyleneoxide modified polydimethylsiloxane and nonionic surfactants) from Setre Chemical Company (Memphis, Tenn.); and Regulaid (90.6% 2-butoxyethanol, poloxalene, monopropylene glycol) from KALO, Inc. (Overland Park, Kans.).

Many different commercial ornamental crops were obtained from local retailers, or from wholesale nurseries, and transported to a greenhouse for testing. Plants were watered to saturation and allowed to stand and drain for about one hour. Plants were selected for uniformity based on leaf area and arranged in a randomized complete block design, or a completely randomized design, on the greenhouse bench. The plants were sprayed or drenched with water or treatment solution equaling about 5-10% of the pot volume. The plants were held without irrigation until all the plants wilted to a point when they were determined to be unmarketable. The plants were rated daily for the extent of wilting on a scale from 1 for no wilting to 4 for complete wilting. A rating of 2.5 was the point at which a plant was determined to be unmarketable and the previous day was recorded as the marketable life of that plant in days. The plants were rated for the extent of lower leaf yellowing or leaf or flower abscission on a scale from 1 for no yellowing or abscission to 4 for complete yellowing or abscission. A rating of 2.5 was the point at which a plant was determined to be unmarketable.

The present invention may be illustrated by the following representative example.

Example 1

Ornamental bedding plants were treated (sprayed or drenched) with water or 250 ppm abscisic acid (S-ABA; ABA; S-(+)-abscisic acid; +-ABA, (+)-(S)-cis,trans-abscisic acid,(+)-(S)-cis,trans-ABA; S-ABA; (S)-5-(1-hydroxy-2,6, 6,-trimethyl-4-oxo-2-cyclohexen-1-yl)-3-methyl-(2Z,4E)-pentadienoic acid; CAS no. 21293-29-8) and then irrigation was withheld until all the plants wilted. Plants were individually rated on a daily basis for degree of wilting and other undesirable characteristics like leaf yellowing.

In Table 1, plants were drenched with water or a 250 ppm ABA solution, and held in a greenhouse without irrigation.

TABLE 1

Classification of ornamental plants by ABA effects on drought tolerance and potential for undesirable side effects of lower leaf yellowing or leaf or flower abscission.

| Classification[1] | Plant | Market life extension[2] | Lower leaf yellowing[3] | Leaf or flower abscision[4] |
|---|---|---|---|---|
| Favorable | *Celosia* | 2.3 | 1 | 1 |
| Favorable | *Chrysanthemum* | 2.0 | 1 | 1 |
| Favorable | *Coleus* | 2.3 | 1 | 1 |
| Favorable | *Cosmos* | 1.4 | 1 | 1 |
| Favorable | *Cuphea* | 2.3 | 1 | 1 |
| Favorable | *Dianthus* | 1.6 | 1 | 1 |
| Favorable | *Euryops* | 3.3 | 1 | 1 |
| Favorable | *Hydrangea* | 3.4 | 1 | 1 |
| Favorable | *Impatiens* | 2.0 | 1 | 1 |
| Favorable | *Lantana* | 2.4 | 1 | 1 |
| Favorable | Marigold | 1.9 | 1 | 1 |
| Favorable | New Guinea *Impatiens* | 3.3 | 1 | 1 |
| Favorable | *Pentas* | 2.8 | 1 | 1 |
| Favorable | *Petunia* | 3.5 | 1.9 | 1 |
| Favorable | *Salvia* | 1.9 | 1 | 1 |
| Favorable | Snapdragon | 1.5 | 1.3 | 1 |
| Unfavorable | *Agapanthus* | 0 | 2 | 1 |
| Unfavorable | Alyssum | 0 | 3.5 | 1 |
| Unfavorable | *Calibrachoa* | 0 | 3 | 1 |
| Unfavorable | *Gazania* | 0 | 3 | 1 |
| Unfavorable | *Lobelia* | 2.5 | 3 | 2.5 |
| Unfavorable | Pansy | 1.6 | 3 | 1 |
| Unfavorable | Poinsettia | 2.0 | 3 | 2.5 |
| Unfavorable | Rose | 0 | 4 | 1 |
| Unfavorable | *Vinca* | 2.5 | 2.5 | 3 |

[1]Classification: Favorable = increased market life due to delayed wilting without the occurrence of unmarketable lower leaf yellowing or abscission, Unfavorable = presence of unmarketable lower leaf yellowing or abscission.
[2]Market life extension = days of additional market life compared to control plants due to delayed wilting.
[3]Lower leaf yellowing = average rating where 1 = no yellowing, 2.5 = unmarketable due to lower leaf yellowing, and 4 = severe lower leaf yellowing.
[4]Leaf or flower abscission = average rating where 1 = no leaf or flower abscission, 2.5 = unmarketable due to leaf or flower abscission, and 4 = severe leaf or flower abscission.

Many bedding plants like New Guinea Impatiens are very favorable candidates for ABA application because treated plants have much greater drought tolerance without any noticeable undesirable side effects. Other plants like Pansy are not favorable candidates for ABA application because even though the treated plants are more drought tolerant the undesirable effect of ABA-induced leaf yellowing often occurs. Other plants like Vinca are not favorable candidates for ABA application because even though the treated plants are more drought tolerant the undesirable effect of flower abscission often occurs. Still other plants like Calibrachoa are not favorable candidates because undesirable side effects like severe leaf yellowing occur before wilting symptoms develop in the control and treated plants.

The invention claimed is:

1. A method for extending the market life of an ornamental plant selected from the group consisting of Impatiens, New Guinea Impatiens and Pentas comprising applying from about 10 ppm to about 1,000 ppm of abscisic acid or salts thereof to said plant by spraying or drenching, wherein said plant exhibits decreased wilting while exhibiting low levels of leaf yellowing and/or leaf or flower abscission.

2. The method of claim 1 wherein the ornamental plant is New Guinea Impatiens.

3. The method of claim 1 wherein the ornamental plant is Impatiens.

4. The method of claim 1 wherein the ornamental plant is Pentas.

\* \* \* \* \*